(12) United States Patent
Kim et al.

(10) Patent No.: US 7,392,689 B2
(45) Date of Patent: Jul. 1, 2008

(54) SAMPLE COLLECTION APPARATUS FOR ANALYSIS OF AIR POLLUTION COMPRISING MOISTURE PRETREATMENT MEANS

(75) Inventors: Jo Chun Kim, Seoul (KR); Ki Joon Kim, Seoul (KR); Ji Yong Kim, Seoul (KR)

(73) Assignee: Konkuk University Industrial Cooperation Corporation (KR)

( * ) Notice: Subject to any disclaimer, the term of this patent is extended or adjusted under 35 U.S.C. 154(b) by 0 days.

(21) Appl. No.: 11/712,190

(22) Filed: Feb. 28, 2007

(65) Prior Publication Data
US 2007/0151326 A1    Jul. 5, 2007

Related U.S. Application Data

(63) Continuation of application No. PCT/KR2005/003688, filed on Nov. 3, 2005.

(30) Foreign Application Priority Data
Nov. 3, 2004    (KR) .................. 10-2004-0088554

(51) Int. Cl.
*G01N 19/10* (2006.01)
(52) U.S. Cl. .................................... 73/31.02
(58) Field of Classification Search ........... 73/31.02, 73/31.07, 863.12
See application file for complete search history.

(56) References Cited

U.S. PATENT DOCUMENTS

| | | | |
|---|---|---|---|
| 5,872,305 A | 2/1999 | Springmann | |
| 5,970,804 A | 10/1999 | Robbat, Jr. | |
| 6,353,225 B1 | 3/2002 | Strzoda et al. | |
| 6,418,781 B1 * | 7/2002 | Nishina et al. | 73/23.35 |
| 6,494,077 B2 * | 12/2002 | Aoyama et al. | 73/23.34 |
| 6,815,670 B2 * | 11/2004 | Jenkins et al. | 250/286 |
| 7,087,434 B2 | 8/2006 | Chen et al. | |

* cited by examiner

*Primary Examiner*—Hezron E. Williams
*Assistant Examiner*—John Fitzgerald
(74) *Attorney, Agent, or Firm*—Knobbe Martens Olson & Bear LLP

(57) ABSTRACT

Disclosed herein is a sample collection apparatus which includes a pretreatment unit arranged in front of a sample collection section to remove moisture, a first Peltier trap positioned at the lower side of the pretreatment unit to perform cooling condensation and thermal desorption, a switching valve connected to the rear of the pretreatment unit to determine flow paths through first, second, third and fourth ports, a sample collection section arranged at the rear of the switching valve to collect samples, a second Peltier trap positioned at the lower side of the sample collection section to perform thermal desorption, a first air pump connected to the second port of the switching valve to intake air, a second air pump connected to the rear of the sample collection section to intake and exhaust air, and a sample analyzer connected to the fourth port of the switching valve to analyze the samples.

8 Claims, 4 Drawing Sheets

[Fig. 1]
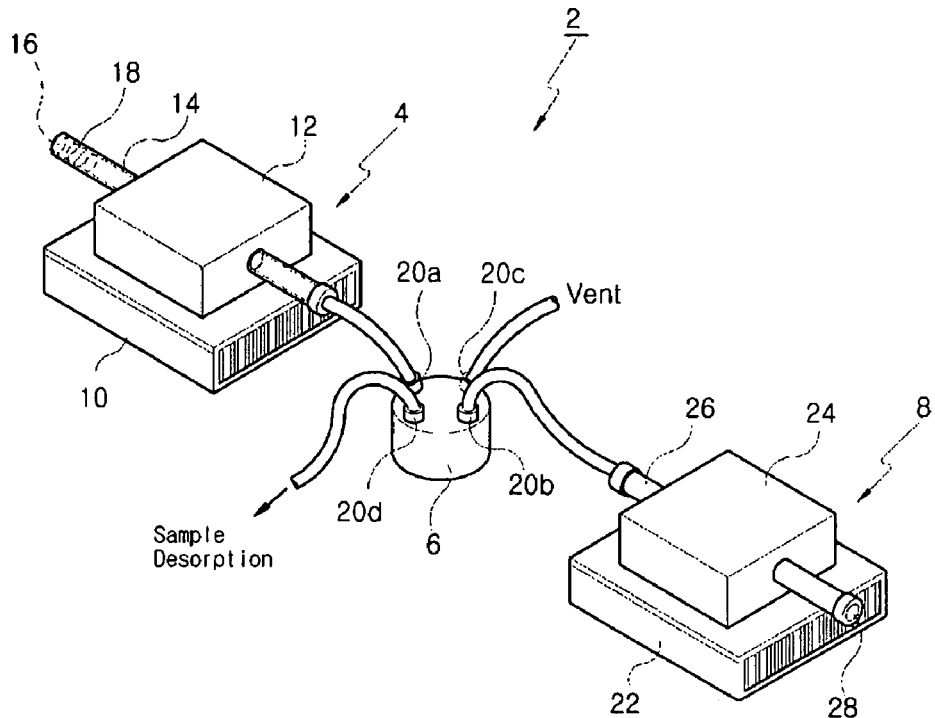
[Fig. 2]
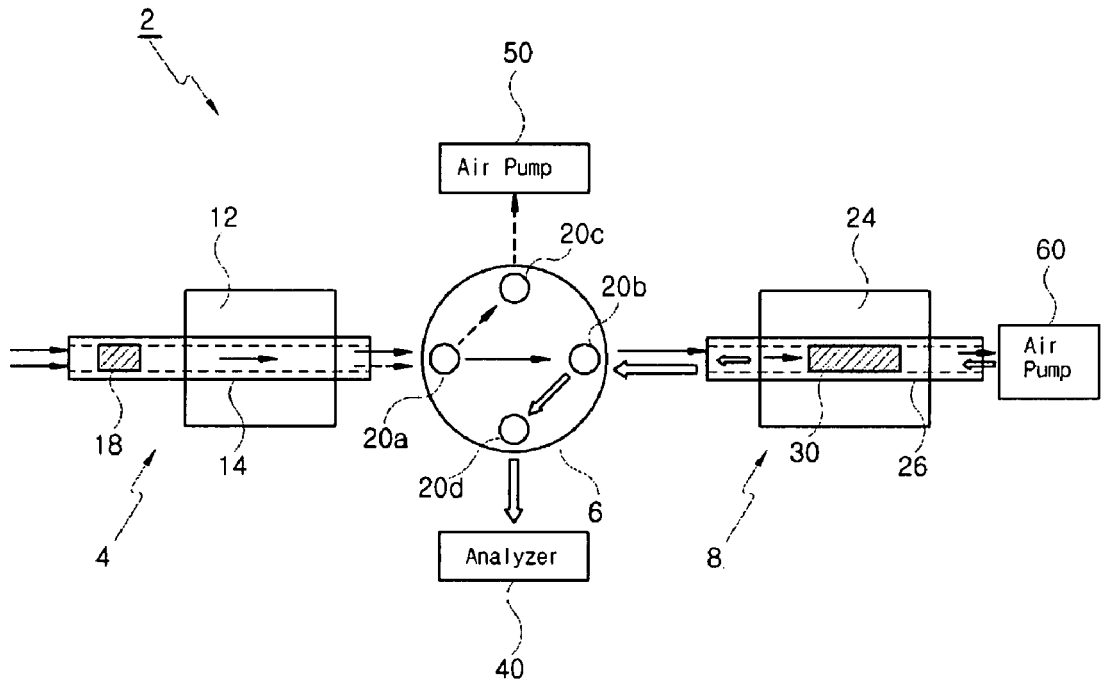

[Fig. 3]
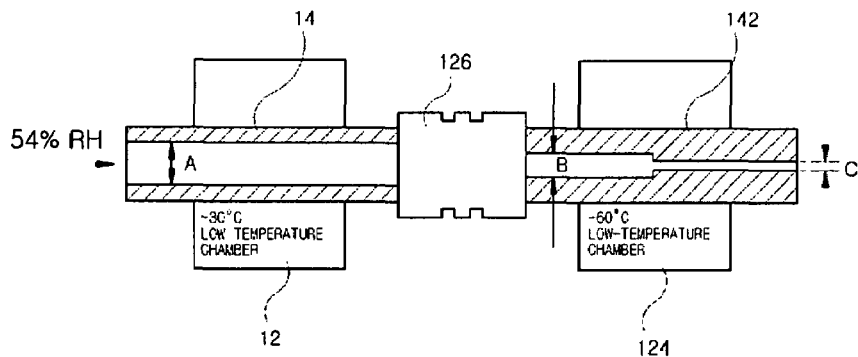
[Fig. 4]
| PARTICULARS | Amount of Moisture Collected in Low-temperature(-30°C) trap | Amount of Moisture Collected in Low-temperature(-60°C) trap |
|---|---|---|
| 1 Cycle | 10.38 | 0.95 |
| 2 Cycle | 9.47 | 0.91 |
| 3 Cycle | 11.28 | 1.03 |
| mean | 10.38 | 0.96 |
| RSD | 8.7 | 6.3 |
| Percentage (%) | 92 | 8 |

[Fig. 5]
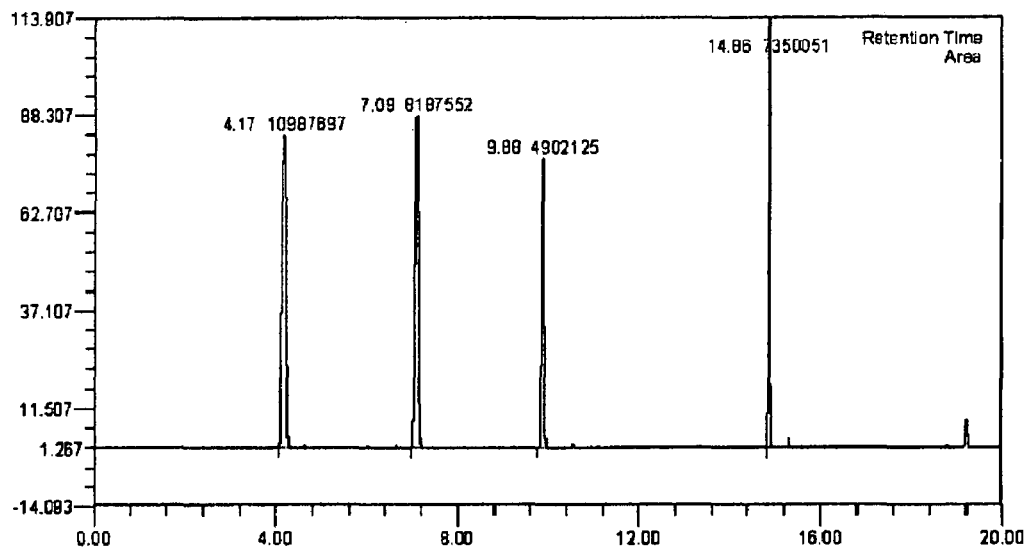
[Fig. 6]
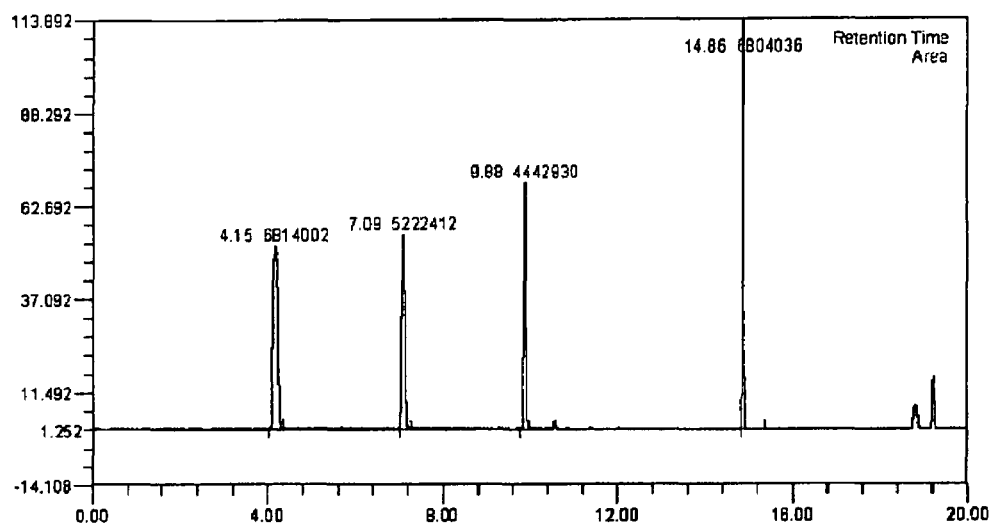

[Fig. 7]
| MATERIALS | H2S | MM | DMS | DMDS |
|---|---|---|---|---|
| CONCENTRATION(ppb) | 0.25 | 1.04 | 0.91 | 0.84 |
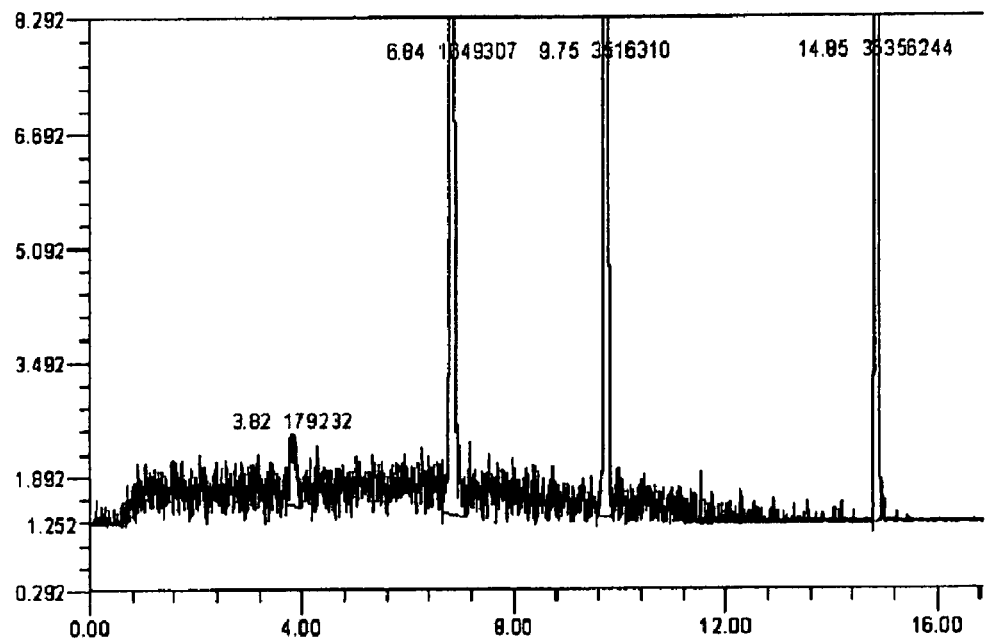

SAMPLE COLLECTION APPARATUS FOR ANALYSIS OF AIR POLLUTION COMPRISING MOISTURE PRETREATMENT MEANS

CROSS-REFERENCE TO RELATED PATENT APPLICATIONS

This application is a continuation application under 35 U.S.C. § 365(c) of International Application No. PCT/KR2005/003688, filed Nov. 3, 2005 designating the United States. International Application No. PCT/KR2005/003688 was published in English as WO2006/049434 A1 on May 11, 2006. This application further claims the benefit of the earlier filing dates under 35 U.S.C. § 365(b) of Korean Patent Application No. 10-2004-0088554 filed Nov. 3, 2004. This application incorporates herein by reference the International Application No. PCT/KR2005/003688 including the International Publication No. WO2006/049434 A1 and the Korean Patent Application No. 10-2004-0088554 in their entirety.

BACKGROUND

1. Field

The present invention relates to a sample collection apparatus for analysis of air pollution comprising moisture pretreatment means, and more particularly to a sample collection apparatus for analysis of air pollution comprising moisture pretreatment means in which a Peltier trap is disposed below a cooling tube to enable accurate control of temperature so that moisture removal and sample collection are facilitated, thus achieving maximized moisture removal effects and rapid collection of stable samples.

2. Discussion of Background Technology

As is well known, automatic analyzers are currently used to collect and analyze volatile organic compounds (VOCs) or malodorous substances. Analysis for the concentrations of particulate materials using automatic analyzers is conducted by measuring the difference in the weight of a filter before and after collection of particulate materials, or by irradiating a filter after collection of particulate materials with light and measuring the amount of light passing through the filter. In addition, analysis of ingredients, such as heavy metals, adsorbed to a filter is conducted by the dissolving the collected ingredients by various pretreatments, including acid treatment and heating.

SUMMARY

An aspect of the present invention provides a sample collection apparatus for analysis of air pollution comprising moisture pretreatment means in which a Peltier trap is disposed below a cooling tube to enable accurate control of temperature so that moisture removal and sample collection are facilitated, thus achieving maximized moisture removal effects and rapid collection of stable samples.

In accordance with an embodiment of the present invention, there is provided a sample collection apparatus for analysis of air pollution comprising moisture pretreatment means, the sample collection apparatus comprising: a pretreatment unit arranged in front of a sample collection section to remove moisture; a first Peltier trap positioned at the lower side of the pretreatment unit to perform cooling condensation and thermal desorption; a switching valve connected to the rear of the pretreatment unit to determine flow paths through first, second, third and fourth ports; a sample collection section arranged at the rear of the switching valve to collect samples; a second Peltier trap positioned at the lower side of the sample collection section to perform thermal desorption; a first air pump connected to the second port of the switching valve to intake air; a second air pump connected to the rear of the sample collection section to intake and exhaust air; and a sample analyzer connected to the fourth port of the switching valve to analyze the samples.

Preferably, the pretreatment unit is provided with a glass tube in the interior periphery of the pretreatment unit to cool and condense moisture.

Preferably, the sample collection section is provided with a glass tube connected to the switching valve to collect samples.

Preferably, the first Peltier trap positioned at the lower side of the pretreatment unit is cooled to remove moisture from contaminated air.

Preferably, the first Peltier trap positioned at the lower side of the pretreatment unit is heated to remove the trapped moisture after completion of sample collection in the sample collection section.

Preferably, the second Peltier trap positioned at the lower side of the sample collection section is heated to desorb the samples after completion of sample collection in the sample collection section.

Preferably, the sample collection apparatus according to an embodiment of the present invention further comprises a cotton layer formed within the glass tube of the pretreatment unit to primarily remove moisture.

Preferably, the sample collection apparatus according to an embodiment of the present invention further comprises an adsorbent layer provided within the glass tube of the sample collection section to adsorb the samples.

BRIEF DESCRIPTION OF THE DRAWINGS

The above and other aspects, features and other advantages of the present invention will be more clearly understood from the following detailed description taken in conjunction with the accompanying drawings, in which:

FIG. 1 is a perspective view showing the structure of a sample collection apparatus for analysis of air pollution comprising moisture pretreatment means according to an embodiment of the present invention;

FIG. 2 is a structural view of a sample collection apparatus for analysis of air pollution comprising moisture pretreatment means according to an embodiment of the present invention;

FIG. 3 is a view showing the state wherein moisture is treated using a sample collection apparatus for analysis of air pollution comprising moisture pretreatment means according to an embodiment of the present invention;

FIG. 4 is a table showing data of moisture removal efficiency obtained using a sample collection apparatus for analysis of air pollution comprising moisture pretreatment means according to an embodiment of the present invention;

FIG. 5 is a chromatogram taken after removal of moisture from contaminated air having a relative humidity of 55% using a sample collection apparatus for analysis of air pollution comprising moisture pretreatment means according to an embodiment of the present invention;

FIG. 6 is a chromatogram taken after removal of moisture from contaminated air having a relative humidity of 100% using a sample collection apparatus for analysis of air pollution comprising moisture pretreatment means according to an embodiment of the present invention; and FIG. 7 is a chromatogram taken after removal of moisture from actual air using a sample collection apparatus for analysis of air pollution comprising moisture pretreatment means according to an embodiment of the present invention.

DETAILED DESCRIPTION OF EMBODIMENTS

Embodiments of the present invention will now be described in more detail with reference to the accompanying drawings.

In a sample collection apparatus for analysis of air pollution, the presence of moisture in samples, particularly volatile organic compounds (VOCs) or malodorous substances, during sample collection using an automatic analyzer may produce large errors in sample analysis.

Particularly, water ($H_2O$), which is a highly polar material, is a major obstacle in the analysis of highly polar malodorous substances or VOCs, such as $H_2S$ and $(CH_3)_2CCl_2$. Thus, treatment of moisture before sample collection or analysis is of particular importance.

U-shaped tubes dipped in a coolant, such as liquid nitrogen, and Nafion dryers may be used to remove moisture. The problems associated with the use of these units are that the U-shaped tubes are clogged and moisture removal efficiency and recovery rate of analytes are low.

Various attempts may be made to prevent clogging of U-shaped tubes by using straight type tubes and uniformly maintaining the inner diameter of the straight type tubes at a constant linear velocity of air at a constant temperature (e.g., −30° C.) so as to allow frost to grow at a constant rate.

Even when straight type tubes are used, however, efficient temperature control is not achieved because moisture is removed by a cooling/condensation process using a coolant, such as liquid nitrogen, as in the use of U-shaped tubes. As a result, moisture removal effects may be negligible and inaccurate sample analysis may be caused.

FIG. 1 is a perspective view showing the structure of a sample collection apparatus for analysis of air pollution comprising moisture pretreatment means according to an embodiment of the present invention. FIG. 2 is a structural view of a sample collection apparatus for analysis of air pollution comprising moisture pretreatment means according to an embodiment of the present invention.

Referring to these figures, the sample collection apparatus 2 for analysis of air pollution according to an embodiment of the present invention is characterized in that it comprises a Peltier trap disposed below a cooling tube to enable accurate control of temperature so that moisture removal and sample collection are facilitated, thus achieving maximized moisture removal effects and rapid collection of stable samples.

Specifically, the sample collection apparatus 2 for analysis of air pollution according to an embodiment of the present invention is largely divided into the following three sections. The first section is a pretreatment section 4 for introducing contaminants present in soil, water and air and removing moisture contained in the contaminants. The second section is a switching valve 6 arranged at the rear of the pretreatment section 4 to optimally switch flow paths. The third section is a sample collection section 8 arranged at the rear of the switching valve 6 to collect the moisture-free contaminants introduced through the switching valve 6.

The pretreatment section 4 includes a Peltier trap 10 having a Peltier module embedded therein and a pretreatment unit 12 arranged on the upper surface of the Peltier trap 10. The pretreatment unit 12 is provided with a glass tube 14 therein to send contaminants to the subsequent section. Further, the glass tube 14 is provided with a cotton layer 18 spaced at a regular interval from a front inlet 16. The cotton layer 18 is means for primary moisture removal. The pretreatment unit 12 is provided with the glass tube 14 therein. As shown in FIG. 3, the pretreatment unit 12 includes a low-temperature (−30° C.) chamber connected to the Peltier trap 10, which is positioned at the lower side of the pretreatment unit 12. The low-temperature chamber is cooled to −30° C. sufficient to remove moisture. An experimental procedure for moisture removal using the Peltier trap 10 will be described in greater detail below.

The Peltier trap 10 is a device using the Peltier effect to cool a particular site. The Peltier trap uses the principle of electronic cooling induced from a heat pumping phenomenon. According to this principle, when a direct current is applied to a circuit including two different metal lines joined to each other, one junction absorbs heat and the other junction generates heat. When the direction of the current is changed, the position of the junctions where heat is generated and absorbed is changed. Accordingly, the Peltier trap 10 can accurately control the temperature of a particular site to the desired degree.

Particularly, the Peltier trap 10 used in an embodiment of the present invention alternately repeats the endothermic and exothermic operations for removing moisture by condensation and instantaneously heating the condensed moisture to a high temperature.

The switching valve 6 arranged at the rear of the Peltier trap 10 to determine flow paths is a diaphragm valve (2-way 6-port), or a solenoid valve for an air actuator. In an embodiment of the present invention, a valve having two ways and four ports (20a, 20b, 20c and 20d) is used to determine flow paths.

The first port 20a is connected to the glass tube 14 of the pretreatment section 4, the second port 20b is connected to a glass tube 26 of the sample collection section 8, the third port 20c is connected to an air pump 50, and the fourth port 20d is connected to a sample analyzer 40.

The sample collection section 8 arranged at the rear of the switching valve 6 is means for collecting the moisture-free sample introduced from the pretreatment section 4. A second Peltier trap 22 is positioned at the lower side of the sample collection section 8. A sample trap 24 is provided on top of the second Peltier trap 22 to collect the samples. The second Peltier trap 22 acts to thermally desorb the samples.

The glass tube 26 is provided within the sample trap 24, and an air pump 60 is connected to the discharge port 28 of the glass tube 26. An adsorbent layer 30, e.g., activated charcoal layer, for sample collection is provided within the glass tube 26.

FIG. 3 is a view showing the state wherein moisture is treated using the sample collection apparatus for analysis of air pollution according to an embodiment of the present invention. FIG. 4 is a table showing data of moisture removal efficiency obtained using the sample collection apparatus for analysis of air pollution according to an embodiment of the present invention.

Referring to these figures, the pretreatment unit 12 of the sample collection apparatus for analysis of air pollution comprising moisture pretreatment means according an embodiment of to the present invention includes a low-temperature chamber whose temperature is maintained at −30° C., which is the lowest temperature that can be reached by the action of the Peltier trap 10. That is, the pretreatment unit 12 of the sample collection apparatus 2 for analysis of air pollution according to an embodiment of the present invention includes the low-temperature (−30° C.) chamber.

The glass tube 14 provided within the low-temperature (−30° C.) chamber is cooled to −30° C. when the Peltier trap 10 for moisture removal is operated, and as a result, moisture contained in contaminated air is condensed and removed, after which the contaminated air is discharged in the backward direction. An experiment for evaluating the moisture removal efficiency of the pretreatment unit 12 is conducted by additionally providing glass tubes 14b having smaller diameters (B and C) than that (A) of the glass tube 14 and a low-temperature chamber 124 whose temperature can be rapidly cooled to −60° C. using liquid nitrogen and dry ice, along with the Peltier trap 22.

The experimental results are shown in FIG. 4. As is evident from the data shown in FIG. 4, the amount of the moisture collected in the Peltier trap 10 of the pretreatment unit 12 is 92% of that of the moisture contained in the introduced contaminated air. Furthermore, when the contaminated air discharged from the low-temperature (−30° C.) chamber was passed through the low-temperature (−60° C.) chamber via an intermediate connection member 126, the moisture is completely removed (i.e. 100%).

In conclusion, since the sample collection apparatus 2 for analysis of air pollution according to an embodiment of the present invention enables accurate control of temperature and control of flow paths, it is more efficient in terms of continuous sample collection. Particularly, considering that liquid nitrogen and dry ice cannot be used for a long period of time and are unsuitable to collect actual outdoor air, the pretreatment unit 12 of the sample collection apparatus according to an embodiment of the present invention is proved to provide advantageous effects.

Hereinafter, the functions and actions of the sample collection apparatus for analysis of air pollution according to an embodiment of the present invention will be explained in detail with reference to the accompanying drawings.

The functions and operation of the sample collection apparatus 2 for analysis of air pollution according to an embodiment of the present invention will be described with reference to FIGS. 1 and 2.

First, contaminated air is introduced into the pretreatment unit 12 via the glass tube 14. Moisture contained in the contaminated air is primarily removed while passing through the cotton layer 18 provided within the glass tube 14. The temperature of the glass tube 14 is rapidly lowered to −30° C. by operating the Peltier trap 10 positioned at the lower side of the pretreatment unit 12 to condense the moisture contained in the contaminated air in the interior periphery of the glass tube 14 and to separate the moisture from the contaminated air.

If the flow passage of the glass tube 14 has a small diameter, the moisture removal is advantageously performed. Taking the load of the air pumps 50 and 60 into consideration, the diameter of the flow passage must be properly adjusted.

Upon sample collection, the switching valve 6 is operated in such a manner that the first port 20a is connected to the second port 20b to form a flow path in the direction of the dark solid arrows. As a result, the pretreatment unit 12 is connected to the sample collection section 8 through the switching valve 6. The contaminated air introduced into the sample collection section 8 through the flow path is free from moisture and is introduced into the glass tube 26 of the sample collection section 8.

The contaminated air introduced into the glass tube 26 is passed through the adsorbent layer 30 provided within the glass tube 26 and is adsorbed on the adsorbent layer 30. For better adsorption, the air pump 60 connected to the discharge port is operated.

Hydrogen sulfide ($H_2S$), methyl mercaptan (MM), dimethyl sulfide (DMS) and dimethyl disulfide (DMDS) contained in the contaminated air are highly reactive with moisture to be transformed into different materials. Moisture removal is essential to accurately analyze the contaminated air. Chromatography can be employed to determine whether moisture is removed or not. Determination of the moisture removal will be explained below.

On the other hand, after the sample collection is completed, the air pump 60 disposed at the rear of the sample collection section 8 is rotated in the reverse direction, the second port 20b of the switching valve 6 is operated to connect to the fourth port 20d, and the first port 20a is operated to connect to the third port 20c.

Thereafter, by operating the air pumps 50 and 60, the contaminated air introduced via the pretreatment unit 12 is conditioned in the direction of the dotted arrows. The samples adsorbed to the adsorbent layer 30 of the sample collection section 8 are thermally desorbed by heating the second Peltier trap 22 positioned at the lower side of the sample collection section 8 to a high temperature. The thermally desorbed samples are discharged by the action of the air pump 60 in the direction of the unfilled arrows, and are then introduced into the sample analyzer 40 through the fourth port 20d of the switching valve 6.

The moisture removal efficiency of the sample collection apparatus 2 for analysis of air pollution according to an embodiment of the present invention is confirmed with respect to FIGS. 5 to 7.

The concentrations of standard gases, including hydrogen sulfide ($H_2S$), methyl, mercaptan (MM), dimethyl sulfide (DMS) and dimethyl disulfide (DMDS), passed through the sample collection apparatus 2 for analysis of air pollution according to an embodiment of the present invention were analyzed by chromatography. As a result, the chromatogram shown in FIG. 5 was obtained at a relative humidity of 55%. In the case of contaminated air, including hydrogen sulfide ($H_2S$), methyl mercaptan (MM), dimethyl sulfide (DMS), dimethyl disulfide (DMDS) and moisture, corresponding peaks of the ingredients were not clearly observed and split.

Chromatography was performed by passing contaminated air having a relative humidity of 55% through the sample collection apparatus 2 for analysis of air pollution according an embodiment of the present invention. The results are shown in FIG. 5. As can be seen from the chromatogram shown in FIG. 5, distinct peaks are observed.

In addition, chromatography was performed by passing contaminated air having a relative humidity of 100% through the sample collection apparatus 2 for analysis of air pollution according an embodiment of the present invention. The results are shown in FIG. 6. From the results, it was confirmed that the sample collection apparatus 2 for analysis of air pollution according an embodiment of the present invention exhibits a high moisture removal rate, comparable to that obtained in FIG. 5.

FIG. 7 shows analytical results obtained using actual air instead of standard air. Specifically, chromatography was performed by passing actual air through the sample collection apparatus 2 for analysis of air pollution according an embodiment of the present invention. The chromatogram shows that individual peaks are accurately observed.

Although the sample collection apparatus 2 for analysis of air pollution according to an embodiment of the present invention has been disclosed for illustrative purposes, those skilled in the art will appreciate that various modifications, additions and substitutions are possible without departing from the technical spirit of the invention.

As apparent from the above description, according to the sample collection apparatus for analysis of air pollution comprising moisture pretreatment means according to an embodiment of the present invention, since moisture can be almost completely removed using the pretreatment unit before sample collection for analysis of air pollutants, samples can be collected and analyzed in a continuous and rapid manner.

What is claimed is:

1. A sample collection apparatus for analysis of air pollution, the apparatus comprising:
   a pretreatment unit arranged in front of a sample collection section to remove moisture;
   a first Peltier trap positioned at a lower side of the pretreatment unit to perform cooling condensation and thermal desorption;
   a switching valve connected to the pretreatment unit to form at least one flow path between at least two of first, second, third and fourth ports;
   the sample collection section connected to the switching valve to collect samples;
   a second Peltier trap positioned at a lower side of the sample collection section to perform thermal desorption;
   a first air pump connected to the second port of the switching valve to intake air;
   a second air pump connected to the sample collection section to intake and exhaust air; and
   a sample analyzer connected to the fourth port of the switching valve to analyze the samples.

2. The sample collection apparatus of claim 1, wherein the first Peltier trap is configured to cool air to remove moisture therefrom.

3. The sample collection apparatus of claim 1, wherein the first Peltier trap is configured to be heated to remove the trapped moisture after completion of sample collection in the sample collection section.

4. The sample collection apparatus of claim 1, wherein the second Peltier trap is configured to be heated to desorb the samples after completion of sample collection in the sample collection section.

5. The sample collection apparatus of claim 1, wherein the pretreatment unit is provided with a glass tube to cool and condense moisture.

6. The sample collection apparatus of claim 5, further comprising a cotton layer formed within the glass tube of the pretreatment unit to remove moisture from air in the glass tube.

7. The sample collection apparatus of claim 1, wherein the sample collection section is provided with a glass tube connected to the switching valve to collect samples.

8. The sample collection apparatus of claim 7, further comprising an adsorbent layer provided within the glass tube of the sample collection section to adsorb the samples.

* * * * *